United States Patent [19]
Dory

[11] Patent Number: 4,922,917
[45] Date of Patent: May 8, 1990

[54] ULTRASONIC TISSUE CHARACTERIZATION

[75] Inventor: Jacques Dory, Coupvray Esbly, France

[73] Assignee: EDAP International, France

[21] Appl. No.: 231,578

[22] Filed: Aug. 12, 1988

[30] Foreign Application Priority Data

Aug. 14, 1987 [FR] France ................................ 87 11828

[51] Int. Cl.⁵ ................................................ A60B 8/00
[52] U.S. Cl. ............................ 128/660.01; 128/661.03
[58] Field of Search ......................... 128/661.07–661.1, 128/24 A, 715

[56] References Cited

U.S. PATENT DOCUMENTS 4,052,977 10/1977 Kay .................................. 128/661.07
4,792,145 12/1988 Eisenberg et al. .................. 128/715

*Primary Examiner*—Francis Jaworski
*Attorney, Agent, or Firm*—William A. Drucker

[57] ABSTRACT

A tissue characterization device is provided comprising means for transmitting high carrier frequency ultrasonic pulses to the tissues, means for receiving and converting the echos into high frequency electric signals and means for storing said electric signals with a sampling frequency sufficient for the high frequency information which they contain to be correctly recorded, further comprising means for reading the stored information at a rate less than the sampling frequency and such that the high frequency spectrum is transposed into the range of audible frequencies and means for converting the transposed spectrum into a sound signal.

3 Claims, 1 Drawing Sheet

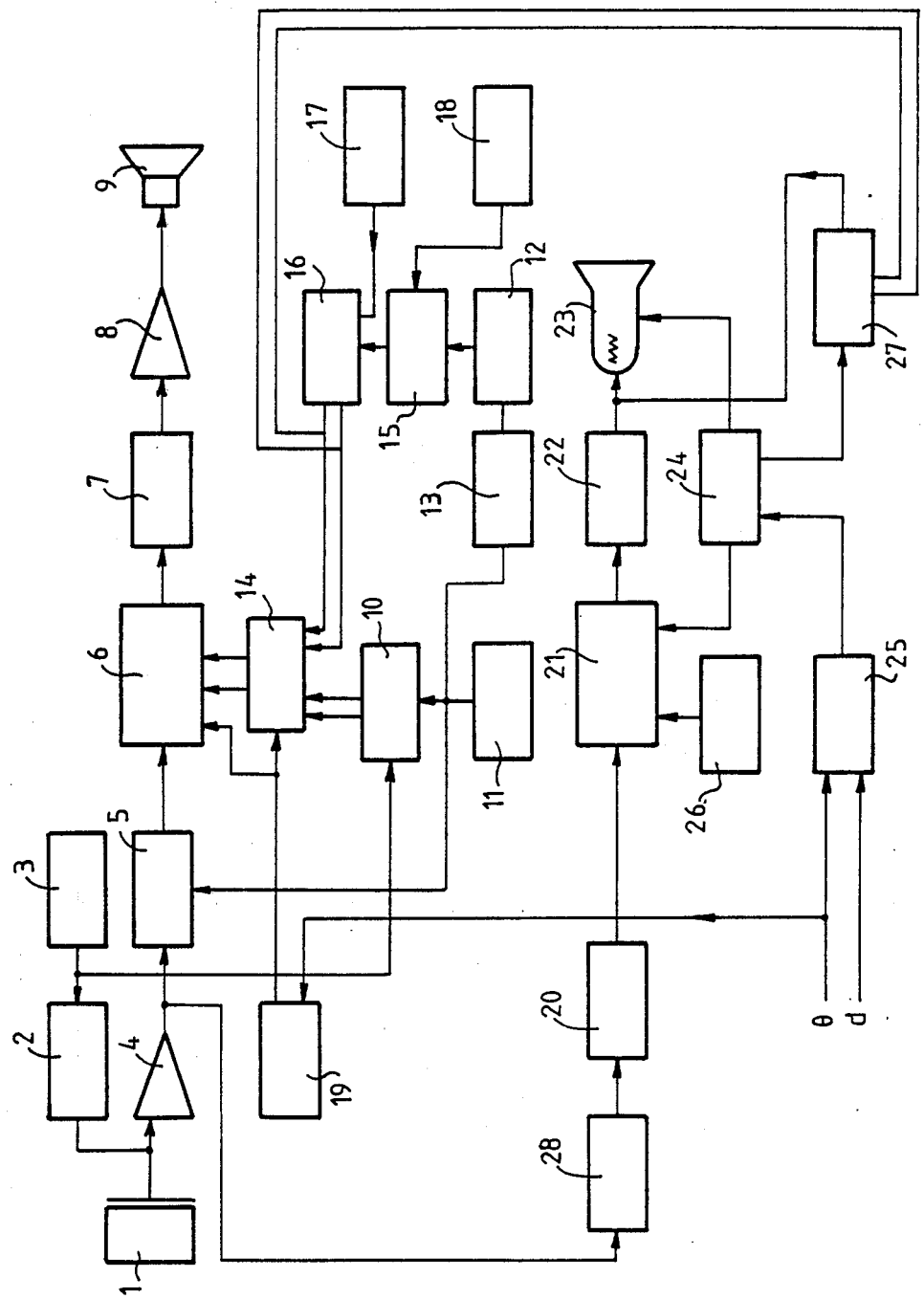

ULTRASONIC TISSUE CHARACTERIZATION

BACKGROUND OF THE INVENTION

It is known to transmit high carrier frequency ultrasonic pulses to a biological tissue and to store the high frequency electric signal received by the transducer after reflection in the tissue. With respect to the transmitted pulse the spectrum of this echo has undergone significant modifications and the Fourier analysis thereof makes it possible to obtain information concerning the structure of the tissue, e.g. for identifying the nature of a tumour, in particular by comparison with the echo spectrums obtained in different tissues or at different echographic observation points. The drawback of this method is the complexity of the apparatus required for carrying out a rapid Fourier analysis and the difficulty of visually interpreting the results.

SUMMARY OF THE INVENTION

The invention proposes transmitting, at different points of the tissue to be characterized, ultrasonic signals with high carrier frequency and to store the high frequency electric signals received after reflection in the tissue and is characterized by reading the information thus stored at a sufficiently slow speed, with respect to the writing speed, so that the frequency band of the resultant signals from such reading is in an audible range and diagnosis by listening to said signals.

BRIEF DESCRIPTION OF THE DRAWINGS

The invention will be better understood from the following description with reference to the following drawings in which:

The single FIGURE is the general diagram of a frequency transposition echography device according to a preferred embodiment of the invention.

MORE DETAILED DESCRIPTION OF THE INVENTION

A transducer 1 is connected, in a way known per se, to a high frequency pulse transmitter 2, itself controlled by a clock 3 and to a high frequency amplifier 4 receiving the echos.

To the output of this amplifier is connected an A-D converter 5 followed by a memory 6 to the output of which are connected a D-A converter 7 and an amplifier 8 which drives a loudspeaker 9 or headphones.

For acquisition the memory is addressed by a counter 10 driven by a clock 11 and, for reading, by a counter 12 driven by clock 11 through a frequency divider 13. The addressing signals generated by counters 10 and 11 are transmitted to the addressing control input of memory 6 by means of a write-read addressing multiplier 14, one input of which is connected directly to the output of counter 10 and another input of which is connected to the output of counter 12 through an address zone selector device 15, followed by an adder 16 adapted for adding to the digital output of device 15 a variable number fixed by a member 17. Device 15 is itself controlled by an adjustment member 18.

Clock 10 further drives converter 5, whereas clock 3 controls the tripping of counter 9 for the acquisition.

A switch 19 controls the setting of multiplexer 14 and of memory 6 alternately for writing or reading, so that writing in the memory takes place during a scan line and reading during the scanning time for the following 5000 or 10000 lines, as will be explained hereafter Preferably, the device which has just been described is associated with a standard echograph, e.g. with sectorial scanning, which includes members 1 to 4 and an additional image buffer memory 21 connected to the output of amplifier 4 through a detector 28 and an A-D converter 20. Memory 21 restores the information which is stored therein to a D-A converter 22, which drives the luminosity control electrode of a cathode ray tube 23.

In a way known per se, a control member 24 delivers the addressing signals for writing in and reading from the memory and the control signals for scanning the screen of the cathode ray tube.

Writing addressing takes place at the scanning rate of the ultrasonic beam, the echography apparatus delivering, in a way known per se, the information $\theta$ and d which correspond, in the case of sectorial scanning, respectively to the instantaneous angular position of the beam and to the distance of the emissive surface of the transducer from the reflecting surface, to a circuit 25 which converts them into memory addresses. A circuit 26, connected to the read-write input of memory 21 provides the desired alternation rate between reading and writing.

The reading addresses delivered by adder 16 are compared with the reading addresses delivered by circuit 24 in a comparator 27. In the case of coincidence, the latter sends an over-brilliance signal to the cathode ray tube 23.

The practical construction of all these circuits which have just been described is within the scope of a man skilled in the art.

The operation of the device will now be described.

It will be assumed that the contents of memory 21 is $256 \times 512$ words, for displaying 256 lines of 512 points on the screen of the cathode ray tube 23. The operation of the conventional echograph 1-2-3-4-20 to 26 is well known: the complete image of the tested organ, which is subjected to angular scanning of the ultrasonic beam, is stored in memory 21 during the acquisition periods and displayed on the screen during the reading periods.

It will be supposed that the high emission frequency is 5 MHz and that probing takes place up to a depth of 150 mm for example.

The ultrasonic echos will comprise components which at most may go up to a frequency of 10 MHz and, to store such components, the sampling frequency will have to be 20 MHz (frequency of clock 11, much higher than that of clock 3 which is for example between 2 and 8 kHz).

By using a memory 6 of $2^{12} = 4096$ words for example, the high frequency information received may be stored therein during the 204.8 $\mu$s which follow the emission pulse, which corresponds substantially to the desired depth, so to a complete scanning line.

Divider 13 divides the frequency of clock 1 1 by a rate between 5000 and 10,000 for example, so that the frequency spectrum of the output signal of the memory will be brought back to 1 to 2 kHz or 0.5 to 1 kHz depending on the division rate.

Such frequencies are audible and the human ear is perfectly capable of qualitatively estimating very small modifications of an audible frequency spectrum.

The assembly 15–18 may be simply formed as a multiposition switch which grounds one or more of the most significant outputs of counter 12 so as to obtain only the first 128, 256 or 512 addresses. In the example described, this assembly will be set at 512, so that the line portion read in memory 6 has the same number of words as the contents of a complete line of memory 21.

The addition to each address thus selected of a number fixed by member 17 makes it possible to position the selected addressing window at will in any one of the eight zones of memory 6, each containing the information corresponding to ⅛ of a line.

For a given position of the addressing window, comparator 27 permanently compares the reading addresses of memories 6 and 21 and thus trips the over-brilliance of an eighth of a line on the screen. Member 19, at the end of the scanning of a line, switches memory 6 to reading and the reading lasts for example as long as the scanning of the next 10,000 lines, namely about 2 seconds. At the end of reading, member 19, which receives information of the value of $\theta$ waits until the scanning has reached the line which follows that previously read so as to switch memory 6 back to writing The construction of such a circuit 13 is within the scope of a man skilled in the art and other methods of using the apparatus could be envisaged.

It goes without saying that different modifications may be made to the device illustrated without departing from the spirit of the invention.

What is claimed is:

1. A static tissue scanning characterization method comprising the steps of:
   (a) transmitting ultrasonic pulses with high carrier frequency to biological tissue to be characterized,
   (b) receiving and storing high frequency pulses as signals reflected from within the tissue;
   (c) examining deformations undergone by the transmitted and reflected frequency spectrum,
   (d) transposing the frequency of the reflected spectrum into the range of audible frequencies, and
   (e) listening to the transposed spectrum.

2. A device for transmitting high carrier frequency ultrasonic pulses to tissue, comprising:
   (a) means receiving and converting echoes into electric signals,
   (b) means storing said signals with a sampling frequency sufficient for information which they contain to be stored,
   (c) means reading said stored signals at a rate less than sampling frequency so that the spectrum is transposed to audible frequencies, and
   (d) means converting said spectrum to sound.

3. The device as claimed in claim 2, further comprising a member for detecting said high frequency electric signals, means for storing the detected signals corresponding to a complete image of a region of a tissue obtained by scanning of the transmitted ultrasonic beam and means for displaying the stored image, wherein said means for storing the high frequency signals are adapted for storing the information corresponding to a scanning line, said means for reading the stored information are arranged for reading a selected addressing zone of adjustable width and position corresponding to a given portion of the scanning line, and said means for storing a complete image comprise a comparator for comparing the addresses of said selected zone and the reading addresses of the image, whereas the display means comprise means for displaying with overbrilliance the line portion which corresponds to the coincidence of said addresses.

* * * * *